US008833168B2

(12) United States Patent  (10) Patent No.: US 8,833,168 B2
Kitazawa et al.  (45) Date of Patent: Sep. 16, 2014

(54) ULTRASONIC INSPECTION DEVICE AND ULTRASONIC INSPECTION METHOD

(75) Inventors: So Kitazawa, Mito (JP); Naoyuki Kono, Mito (JP); Atsushi Baba, Tokai (JP)

(73) Assignee: Mitsubishi Hitachi Power Systems, Ltd., Kanagawa (JP)

( * ) Notice: Subject to any disclaimer, the term of this patent is extended or adjusted under 35 U.S.C. 154(b) by 811 days.

(21) Appl. No.: 12/974,004

(22) Filed: Dec. 21, 2010

(65) Prior Publication Data

US 2011/0164033 A1    Jul. 7, 2011

(30) Foreign Application Priority Data

Jan. 5, 2010  (JP) ................................. 2010-000479

(51) Int. Cl.
| | | |
|---|---|---|
| G01N 29/06 | (2006.01) | |
| G01N 29/44 | (2006.01) | |
| G06T 7/00 | (2006.01) | |
| G01N 29/26 | (2006.01) | |
| G06T 19/00 | (2011.01) | |
| G01S 7/52 | (2006.01) | |
| G01S 15/89 | (2006.01) | |

(52) U.S. Cl.
CPC .... *G01N 29/069* (2013.01); *G06T 2207/10136* (2013.01); *G01S 7/52074* (2013.01); *G01N 2291/106* (2013.01); *G06T 7/001* (2013.01); *G01N 29/262* (2013.01); *G06T 2200/24* (2013.01); *G06T 19/00* (2013.01); *G01S 15/8993* (2013.01); *G06T 2207/30164* (2013.01)
USPC ........................................................ 73/602

(58) Field of Classification Search
USPC .................... 73/602, 641, 634, 267, 628, 627
See application file for complete search history.

(56) References Cited

U.S. PATENT DOCUMENTS 5,475,613 A  *  12/1995  Itoga et al. ...................... 702/39
8,371,171 B2 *  2/2013  Isobe et al. ..................... 73/602
(Continued)

FOREIGN PATENT DOCUMENTS

EP     2 128 609 A1    12/2009
(Continued)

OTHER PUBLICATIONS

McNab et al.; "Role of 3-D graphic in NDT data processing"; IEE Proceedings Science, Measurement & Technology; Jul. 4, 2001; pp. 149-158; vol. 148; No. 4.

(Continued)

*Primary Examiner* — Peter Macchiarolo
*Assistant Examiner* — Rose M Miller
(74) *Attorney, Agent, or Firm* — Mattingly & Malur, PC

(57) ABSTRACT

An ultrasonic inspection device allows position adjustment of three-dimensional inspection data and shape data to be easily performed on a display screen and allows a defect echo and a shape echo to be quickly identified. A calculator generates the three-dimensional inspection data from waveforms stored in a data storage unit. A three-dimensional display unit displays the three-dimensional inspection data generated by the calculator and the three-dimensional shape data on an object to be inspected. The calculator corrects the relative displayed positions of the three-dimensional inspection data and the three-dimensional shape data on the basis of a coordinate system defined by points and a surface that constitute a part of the three-dimensional shape data displayed by the three-dimensional display unit, and causes the three-dimensional display unit to display the three-dimensional inspection data and the three-dimensional shape data while the three-dimensional inspection data and the three-dimensional shape data overlap each other.

6 Claims, 8 Drawing Sheets

(56) References Cited

U.S. PATENT DOCUMENTS

2004/0149021 A1  8/2004  Kessler et al.
2009/0293621 A1  12/2009  Kitazawa et al.

FOREIGN PATENT DOCUMENTS

| | | | |
|---|---|---|---|
| JP | 04249798 A | * | 9/1992 |
| JP | 2006314520 A | * | 11/2006 |
| JP | 2009-288129 A | | 10/2009 |
| WO | WO 2009107746 A1 | * | 9/2009 |

OTHER PUBLICATIONS

M. Kondo et al., Digital signal processing with measurement sensor, Digital Signal Processing Series, vol. 12, pp. 143-186, Jan. 1993.

A. Baba et al., Development of 3-Dimensional Ultrasonic Testing System "3-D Focus-UT", Japan Society of Maintenology, The Fifth Scientific Lecture Meeting, Summary Report, 155 (2008).

A. Potts et al., Presentation and analysis enhancements of the NDT Workbench a software package for ultrasonic NDT data, Review of Progress in Quantitative Nondestructive Evaluation: vol. 19, AIP Conference Proceedings, vol. 509, pp. 741-748 (2000).

* cited by examiner

ULTRASONIC INSPECTION DEVICE AND ULTRASONIC INSPECTION METHOD

BACKGROUND OF THE INVENTION

1. Field of the Invention

The present invention relates to an ultrasonic inspection device and an ultrasonic inspection method, which are one type of nondestructive inspection techniques. The invention more particularly relates to an ultrasonic inspection device that includes an array type ultrasonic probe, and an ultrasonic inspection method in which an array type ultrasonic probe is used.

2. Description of the Related Art

In recent years, constructional materials and the like are inspected by an ultrasonic inspection method. Such a method having being developed more accurately generates an image inside of an object to be inspected in a short time to inspect the inside of the object, as typified by a phased array method and an aperture synthesis method (refer to, for example, Non-Patent Document 1 (Digital signal processing series, volume 12, "Digital signal processing with measurement sensor" pp 143-186, issued by Shokodo, written by Michimasa Kondo, Yukimasa Ohashi, and Akio Jitsumori)).

The phased array method is based on a principle in which an array type ultrasonic probe having a plurality of piezoelectric elements is used and wavefronts of ultrasonic waves transmitted from the piezoelectric elements interfere with each other to form a synthesized wavefront that propagates. Thus, in the phased array method, timings of transmission of ultrasonic waves from the piezoelectric elements are controlled to delay so that timing of each transmission is shifted, thereby enabling control on incident angles of the ultrasonic waves and also focusing of the ultrasonic waves. For reception of ultrasonic waves, incident angles of ultrasonic waves that are reflected, and received by the piezoelectric elements are shifted in timing and is summed, thereby enabling control on the incident angles to be formed when the ultrasonic waves are received and also reception of the ultrasonic waves in focused state, as is the case with the transmission.

A linear scanning method and a sector scanning method are generally known as the phased array method. The linear scanning method is such that piezoelectric elements for a one-dimensional array probe linearly scan an object to be inspected. The sector scanning method is such that a direction in which an ultrasonic wave is transmitted or received is changed within a fan-shaped region. If a two-dimensional array probe that has piezoelectric elements arranged in a matrix pattern is used, ultrasonic waves can be three-dimensionally focused on any position and thereby scanning suitable for an object to be inspected can be performed. Each of the two methods allows ultrasonic waves to be scanned at high speed without moving the ultrasonic probe. Also, each of the two methods allows incident angles of ultrasonic waves and the vertical position at a focal point thereof to be controlled without replacing the ultrasonic probe. These methods are techniques which enable inspection to be performed at high speed with high accuracy.

The aperture synthesis method is based on the following principle: when a piezoelectric element transmits an ultrasonic wave in such a manner that the ultrasonic wave spreads in an object to be inspected and the piezoelectric element receives the reflected ultrasonic wave, a defect that is the source from which the received reflected ultrasonic wave derives is present on a circular arc that has a center thereof at the position of the piezoelectric element (that transmitted and received the ultrasonic wave) and has a radius of a distance that the reflected ultrasonic wave propagates. The piezoelectric element transmits an ultrasonic wave and receives the reflected ultrasonic wave while the position of the piezoelectric element is sequentially changed. The ultrasonic waves received by the piezoelectric element at the positions are calculated by an electronic computer so that the ultrasonic waves are represented by circular arcs. Intersections on the circular arcs are concentrated at the position of a defect that is the source from which the reflected ultrasonic waves derive, whereby the position of the defect is specified. The details of the calculation performed by the electronic computer are described in Non-Patent Document 1.

In the methods in which a probe that has a plurality of piezoelectric elements is used, the probe can three-dimensionally receive an ultrasonic wave signal reflected from a defect without a movement of the probe. However, in order to specify the three-dimensional position of the defect on the basis of the reflected ultrasonic wave signal, the three-dimensional position of the defect is estimated on the basis of a two-dimensional image having multiple reflection intensity distributions of waves reflected at locations that are spatially different from each other. Alternatively, the three-dimensional position of the defect is estimated by converting the reflection intensity distributions into three-dimensional data and then three-dimensionally displaying the three-dimensional data.

When the linear scanning method and the sector scanning method based on phased array methods are adopted, multiple two-dimensional reflection intensity images responsive to known scanning pitches can be acquired. Thus, a direction in which a reflected ultrasonic wave appears can be specified by sequentially selectively displaying the two-dimensional reflection intensity images on a screen. However, these methods have limitations when three-dimensional scanning other than the aforementioned scanning is performed.

To cope with this, advancement in computer technology in recent years has made available a technique for performing interpolation on ultrasonic wave signals reflected and received from multiple directions so that image data that indicates points three-dimensionally arranged in a matrix pattern is generated and displaying the image data by volume rendering or surface rendering. In addition, there is a technique for displaying an image as a three-dimensional point group without conversion of the reflected ultrasonic wave signals into data that indicates points arranged in a matrix pattern. Since the techniques are designed such that the data is stored as three-dimensional inspection data, an inspector can confirm the three-dimensional inspection data in any direction after the measurement (refer to, for example, Non-Patent Document 2 ("Development of 3-Dimensional Ultrasonic Testing System "3D Focus-UT"", Japan Society of Maintenology, The fifth scientific lecture meeting, Summary report, 155 (2008), written by Atsushi Baba, So Kitazawa, Naoyuki Kono, Yuji Adachi, Mitsuru Odakura, and Osamu Kikuchi) and Non-Patent Document 3 (Potts, A; McNab, A.; Reilly D.; Toft, M., "Presentation and analysis enhancements of the NDT Workbench a software package for ultrasonic NDT data", REVIEW OF PROGRESS IN QUANTITATIVE NONDESTRUCTIVE EVALUATION: Volume 19. AIP Conference Proceedings, Volume 509, pp. 741-748 (2000)).

However, it is difficult to determine, only on the basis of such three-dimensional inspection data, whether or not a wave that corresponds to a peak of a reflection intensity distribution is a wave reflected on an end surface or boundary surface of an object to be inspected or is a wave reflected on a defect. Especially, it is difficult even for an experienced inspector to make such a determination for inspection of an object having a complex shape, since reflected ultrasonic wave signals (shape echoes) dependent on the shape of the object appear in great numbers. Thus, software has been developed that allows data (three-dimensional shape data) on the three-dimensional shape of an object (to be inspected) to be displayed together with three-dimensional inspection data. By overlapping and comparing the two types of the data using this software, it is possible to easily determine whether an ultrasonic wave signal is a shape echo or an echo (defect echo) generated from a defect. Data generated by a general-purposed computer aided design (CAD) system is read and used for three-dimensional shape data in many cases (refer to, for example, Non-Patent Documents 2 and 3).

SUMMARY OF THE INVENTION

However, the three-dimensional inspection data and the three-dimensional shape data are generated using different coordinate systems. In order to overlap and display the three-dimensional inspection data and the three-dimensional shape data, it is necessary to perform positioning correction by moving the three-dimensional inspection data or the three-dimensional shape data to an appropriate position on a display screen. If the correction is not appropriately performed, it is not possible to confirm the correlation between the three-dimensional inspection data and the three-dimensional shape data. Thus, it is not possible to identify a shape echo and a defect echo. In a conventional technique, an inspector performs a positioning correction operation using a display device so as to change coordinate values of the three-dimensional inspection data and coordinate values of the three-dimensional shape data on the basis of numerical information on the relative positions of a probe and an object (to be inspected). This operation is repeatedly performed until identification of a shape echo and a defect echo can be attained; it disadvantageously takes much time to identify the echoes.

An object of the present invention is to provide an ultrasonic inspection device and an ultrasonic inspection method, which allow position adjustment of three-dimensional inspection data and three-dimensional shape data to be easily performed on a display screen and allow a defect echo and a shape echo to be quickly identified.

(1) In order to accomplish the aforementioned object, an ultrasonic inspection device includes: an ultrasonic probe that includes a plurality of piezoelectric elements; a pulser that supplies transmission signals to the respective piezoelectric elements of the ultrasonic probe; a receiver that receives signals from the respective piezoelectric elements of the ultrasonic probe; a delay time controller that sets delay times to the transmission signals to be supplied to the piezoelectric elements and sets delay times to the signals received by the piezoelectric elements, the delay times set to the transmission signals being different from each other, the delay times set to the received signals being different from each other; a data storage unit that stores the waveforms of ultrasonic waves received by the ultrasonic probe; a calculator that is provided for image processing and generates three-dimensional inspection data from the waveforms stored in the data storage unit; a three-dimensional display unit that displays three-dimensional shape data on an object to be inspected and the three-dimensional inspection data generated by the calculator; and a positioning correction section that corrects the relative positions of the displayed three-dimensional shape data and the displayed three-dimensional inspection data on the basis of a coordinate system defined by points and a surface that constitute a part of the three-dimensional shape data displayed by the three-dimensional display unit, the positioning correction section being used for displaying the three-dimensional shape data and the three-dimensional inspection data while the three-dimensional shape data and the three-dimensional inspection data overlap each other.

In the ultrasonic inspection device, it is possible to easily position the three-dimensional inspection data and the three-dimensional shape data on a display screen and quickly identify a defect echo and a shape echo.

(2) In the ultrasonic inspection device described in the aforementioned item (1), it is preferable that the surface that constitutes a part of the three-dimensional shape data correspond to a surface on which the ultrasonic probe has been placed in order to store the waveforms of the ultrasonic waves.

(3) The ultrasonic inspection device described in the aforementioned item (1) preferably further includes a mouse that is connected to the calculator, wherein the points and the surface that constitute the part of the three-dimensional shape data are selected with the mouse.

(4) In order to accomplish the aforementioned object, an ultrasonic inspection method includes the steps of: correcting the relative displayed positions of three-dimensional shape data and three-dimensional inspection data on the basis of a coordinate system defined by points and a surface that constitute a part of the three-dimensional shape data, the three-dimensional inspection data being generated from a plurality of waveforms of ultrasonic waves received by an ultrasonic probe; and displaying the three-dimensional shape data and the three-dimensional inspection data while the three-dimensional shape data and the three-dimensional inspection data overlap each other.

In the method, it is possible to easily position the three-dimensional inspection data and the three-dimensional shape data on a display screen and quickly identify a defect echo and a shape echo.

(5) The method described in the aforementioned item (4) preferably further includes the steps of: defining a Z direction that is perpendicular to an inspection surface on which the ultrasonic probe has been placed, the inspection surface being selected from the three-dimensional shape data displayed on a three-dimensional display screen; redisplaying the three-dimensional shape data and the three-dimensional inspection data after positive and negative sides of the three-dimensional inspection data displayed on the three-dimensional display screen in the Z direction match positive and negative sides of the three-dimensional shape data displayed on the three-dimensional display screen in the Z direction with a surface that includes an incident point in the three-dimensional inspection data match the inspection surface of the three-dimensional shape data; setting a Z axis that has an origin that is a first point located on and selected from the three-dimensional shape data; moving the three-dimensional inspection data or the three-dimensional shape data in parallel so that the origin of the three-dimensional inspection data matches the first point; setting an X axis that has an origin that is the first point, the X axis extending on a line that connects the first point to a second point located on and selected from the three-dimensional shape data; setting a Y axis so that the X, Y and Z axes form a right handed coordinate system; rotating the three-dimensional inspection data or the three-dimensional shape data relative to the other data around the Z axis on the basis of input information on an rotational angle and updating the display; and moving the three-dimensional inspection data or the three-dimensional shape relative to the other data in parallel along the X, Y and Z axes on the basis of input information on the amount of the parallel movement and updating the display.

(6) In the method described the aforementioned item in (5), it is preferable that the surface that constitute a part of the three-dimensional shape data correspond to a surface on which the ultrasonic probe has been placed in order to store the waveforms of the ultrasonic waves.

(7) In the method described the aforementioned item in (5), it is preferable that the points and the surface that constitute the part of the three-dimensional shape data be selected with a mouse.

According to the present invention, it is possible to easily perform position adjustment of the three-dimensional inspection data and the three-dimensional shape data on the display screen and quickly identify a defect echo and a shape echo.

DESCRIPTION OF THE PREFERRED EMBODIMENTS

The configuration and operations of an ultrasonic inspection device according to an embodiment of the present invention are described below with reference to FIGS. 1 to 10.

First, the entire configuration of the ultrasonic inspection device according to the present embodiment is described with reference to FIGS. 1 to 3.

Figure 1:
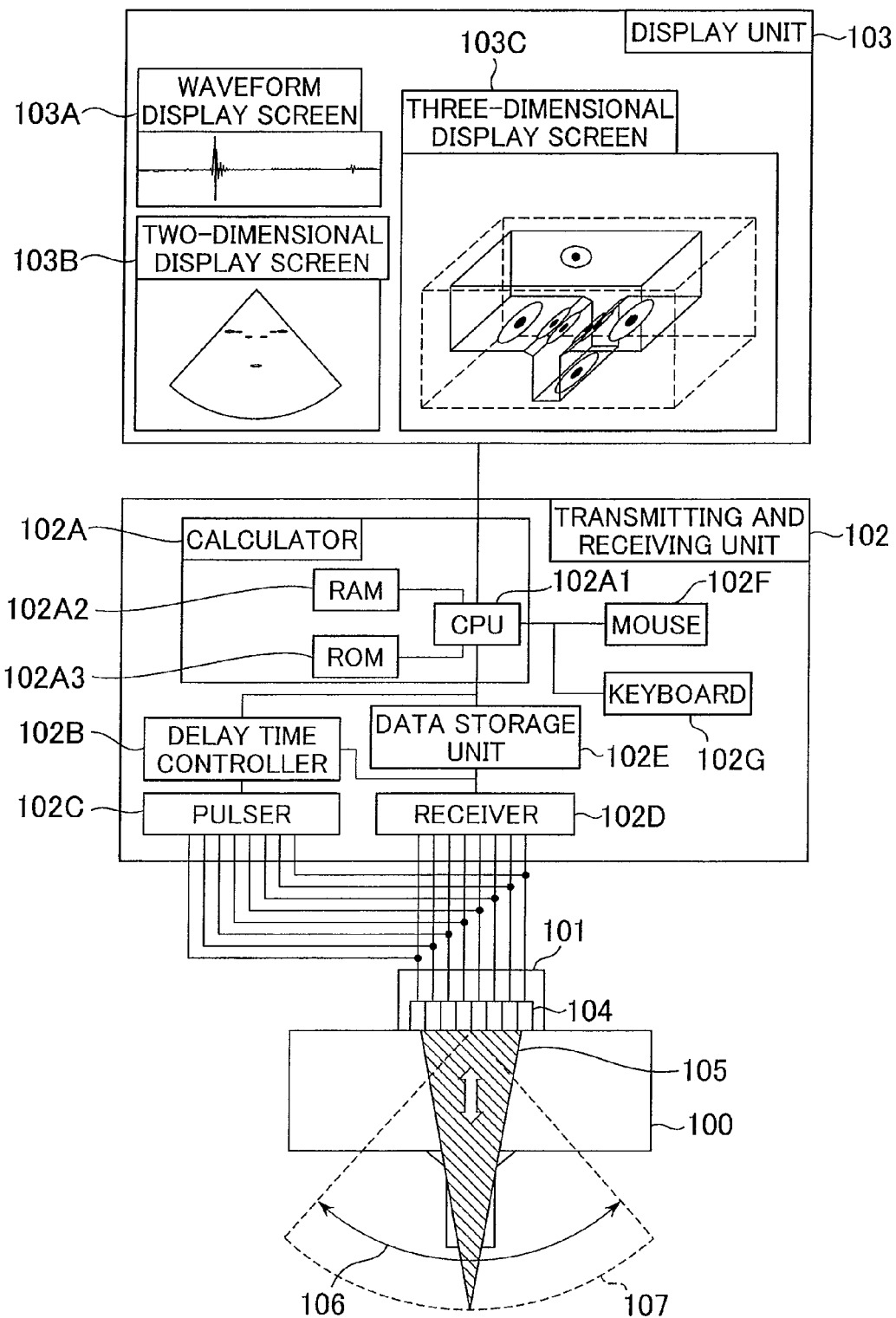
FIG. 1 is a block diagram showing the entire configuration of an ultrasonic inspection device according to an embodiment of the present invention.

FIG. 1 is a block diagram showing the entire configuration of the ultrasonic inspection device according to the present embodiment. FIG. 2 is a diagram showing a first example of a scanning method that is performed by the ultrasonic inspection device according to the present embodiment. FIG. 3 is a diagram showing a second example of the scanning method that is performed by the ultrasonic inspection device according to the present embodiment.

As shown in FIG. 1, the ultrasonic inspection device according to the present embodiment includes an array type ultrasonic probe 101, a transmitting and receiving unit 102 and a display unit 103. The array type ultrasonic probe 101 transmits ultrasonic waves so that the ultrasonic waves are incident on an object 100 to be inspected. The display unit 103 displays received signal and an image (inspection image) on the object 100 to be inspected.

As shown in FIG. 1, the array type ultrasonic probe 101 includes a plurality of piezoelectric elements 104 that each generate and receive an ultrasonic wave. The array type ultrasonic probe 101 is placed on a surface (hereinafter also referred to as an inspection surface) of the object 100 to be inspected. After that, the array type ultrasonic probe 101 receives driving signals from the transmitting and receiving unit 102 and generates ultrasonic waves 105 on the basis of the driving signals. Then, the array type ultrasonic probe 101 causes the generated ultrasonic waves to propagate in the object 100 to be inspected. The array type ultrasonic probe 101 detects, as received signals, the waves reflected from the object 101. The array type ultrasonic probe 101 transmits the received signals to the transmitting and receiving unit 102. In FIG. 1, the array type ultrasonic probe 101 is in direct contact with the object 100 to be inspected. However, the array type ultrasonic probe 101 may be in contact with the object 100 through a wedge made of a material through which an ultrasonic wave can pass.

The transmitting and receiving unit 102 causes the array type ultrasonic probe 101 to transmit and receive ultrasonic waves. The transmitting and receiving unit 102 includes a calculator 102A, a delay time controller 102B, a pulser 102C, a receiver 102D and a data storage unit 102E. The pulser 102C supplies driving signals to the array type ultrasonic probe 101. The receiver 102D processes signals transmitted from the array type ultrasonic probe 101.

The calculator 102A basically includes a CPU 102A1, a RAM 102A2 and a ROM 102A3. A program that controls the CPU 102A1 is written in the ROM 102A3. The CPU 102A1 reads necessary external data from the data storage unit 102E according to the program written in the ROM 102A3. In addition, the CPU 102A1 receives data from the RAM 102A2, executes arithmetic processing on the received data, and outputs the processed data to the data storage unit 102E.

The CPU 102A1 controls the delay time controller 102B, the pulser 102C and the receiver 102D so that the delay time controller 102B, the pulser 102C and the receiver 102D perform necessary operations. The delay time controller 102B controls the timings of outputting driving signals from the pulser 102C and the timings of inputting received signals to the receiver 102D. Thus, the array type ultrasonic probe 101 can perform an operation according to a phased array method.

The operation that is performed by the array type ultrasonic probe 101 according to the phased array method is an operation of controlling incident angles 106 of ultrasonic waves 105 and the depth of a point at which the ultrasonic waves 105 are focused, transmitting the ultrasonic waves 105, and receiving the reflected ultrasonic waves 105. Thus, the receiver 102D receives signals from the array type ultrasonic probe 101 and supplies the received signals to the data storage unit 102E.

As described above, in phased array methods, various types of scanning can be performed by changing delay times. A linear scanning method in which the ultrasonic waves 105 propagate in parallel in order to acquire two-dimensional inspection data is known as one of the phased array methods. In addition, a sector scanning method in which the ultrasonic waves 105 propagate within a sector 107 is known as another one of the phased array methods.

Figure 2:
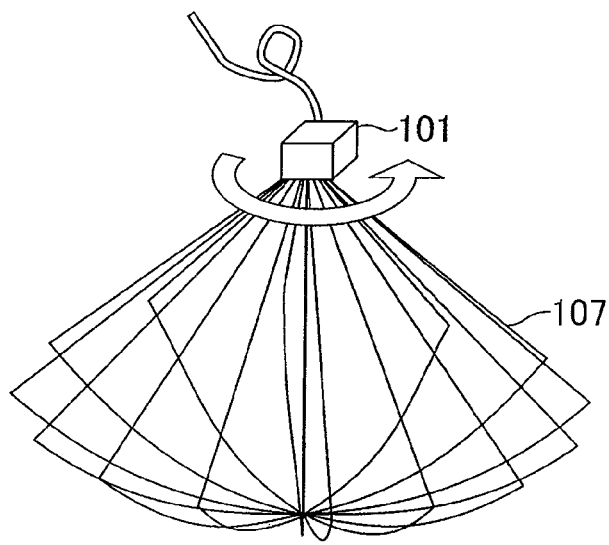
FIG. 2 is a diagram showing a first example of a scanning method that is performed by the ultrasonic inspection device according to the embodiment of the present invention.
Figure 3:
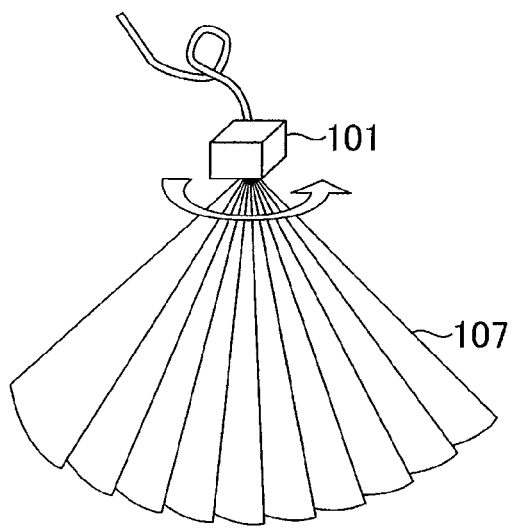
FIG. 3 is a diagram showing a second example of the scanning method that is performed by the ultrasonic inspection device according to the embodiment of the present invention.

For example, as shown in FIG. 2, scanning is performed to acquire three-dimensional inspection data so that the sector 107 is treated as a basic unit and rotated around a central axis of the probe 101. In addition, as shown in FIG. 3, scanning is performed to acquire three-dimensional inspection data so that the sector 107 is moved in a fan-shaped region. Various types of scanning other than the linear scanning and the sector scanning can be performed on the basis of the shape of the object 100 to be inspected.

Signals that are received by performing those types of scanning are transmitted to the data storage unit 102E, stored in the data storage unit 102E as stored data, and transmitted to the calculator 102A. The calculator 102A performs, on the basis of delay times, synthesis processing on the waveforms of the signals received by the piezoelectric elements, performs appropriate interpolation on the waveforms of the signals for the incident angles of the respective ultrasonic waves, and generates two-dimensional inspection data (pixel format inspection data including a two-dimensional square lattice as a unit) or three-dimensional inspection data (voxel format inspection data including a three-dimensional square lattice as a unit). Then, the calculator 102A converts the generated data into an image and causes the display unit 103 to display the image.

The display unit 103 includes a two-dimensional display screen 103B, a three-dimensional display screen 103C and a waveform display screen 103A. The two-dimensional inspection data is displayed on the two-dimensional display screen 103B. The three-dimensional inspection data is displayed on the three-dimensional display screen 103C. The waveform signals of the ultrasonic waves received by the piezoelectric elements are displayed on the waveform display screen 103A. In FIG. 1, the ultrasonic inspection device includes one display unit 103. However, the waveform display screen 103A, the two-dimensional display screen 103B and the three-dimensional display screen 103C may be included in display units, respectively. In this case, the display units are separately provided in the ultrasonic inspection device according to the present embodiment.

Figure 4:
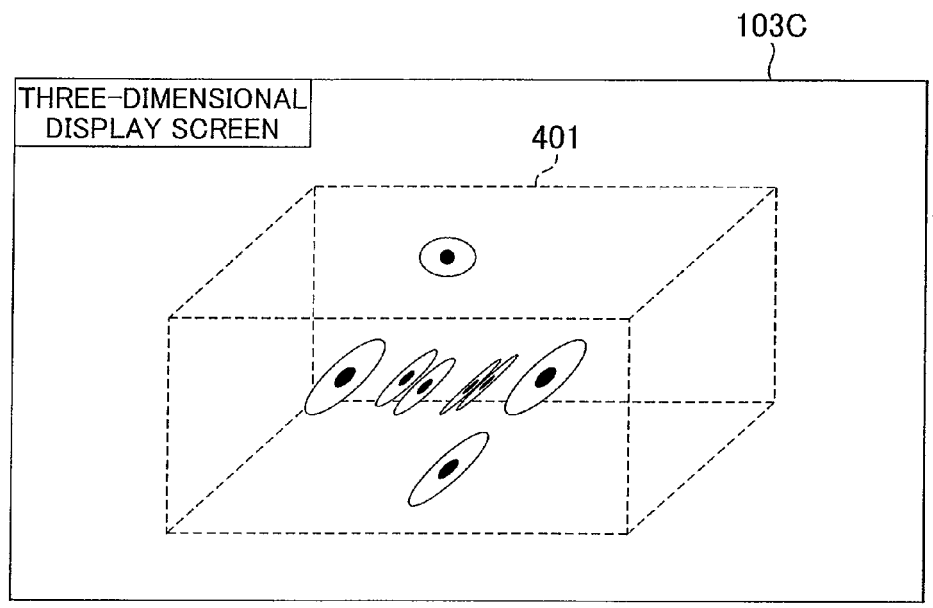
FIG. 4 is a diagram showing an example of an image displayed on a three-dimensional display screen included in the ultrasonic inspection device according to the embodiment of the present invention.
Figure 5:
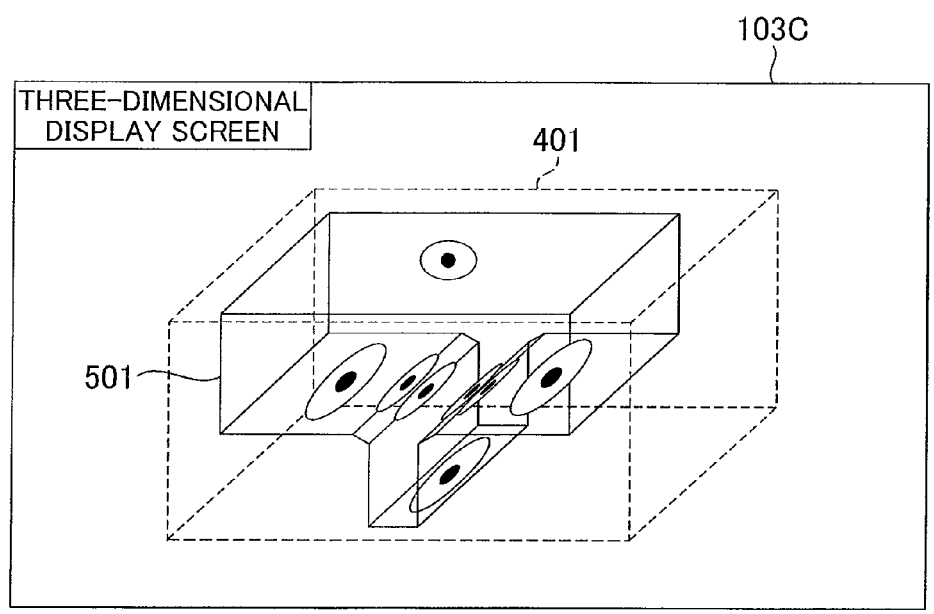
FIG. 5 is a diagram showing an example of an image displayed on the three-dimensional display screen included in the ultrasonic inspection device according to the embodiment of the present invention.
Figure 6:
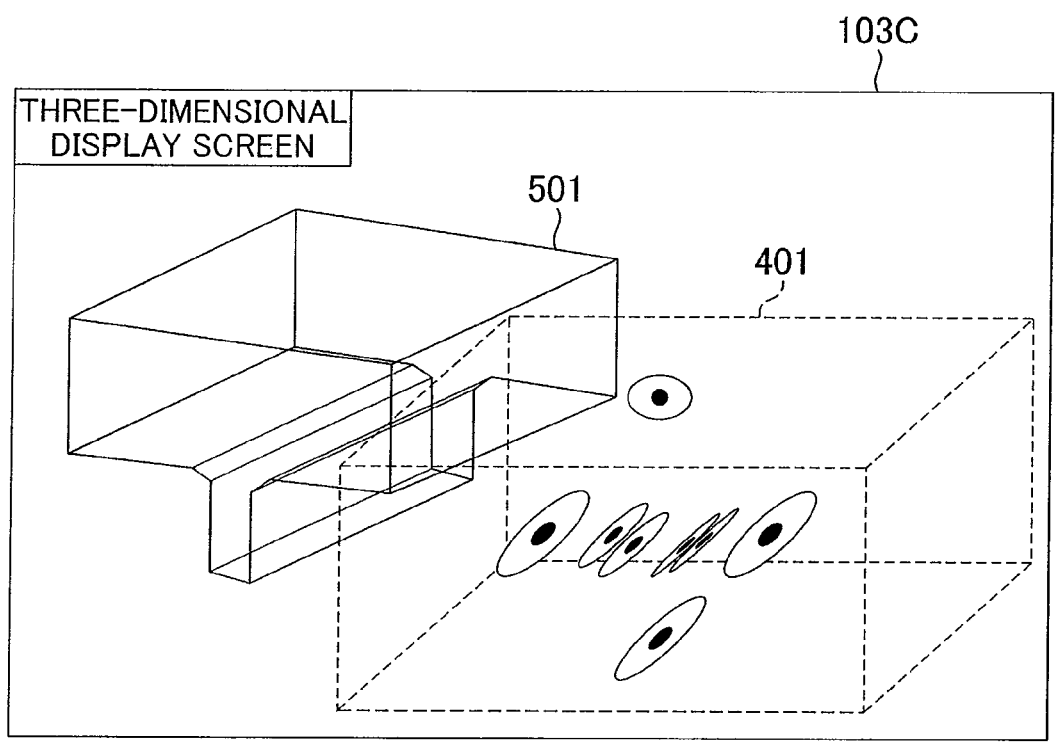
FIG. 6 is a diagram showing an example of an image displayed on the three-dimensional display screen included in the ultrasonic inspection device according to the embodiment of the present invention.

FIGS. 4 to 6 show examples of data displayed on the three-dimensional display screen 103C included in the ultrasonic inspection device according to the present embodiment.

As shown in FIG. 4, three-dimensional inspection data 401 is displayed on the three-dimensional display screen 103C included in the display unit 103. A mouse 102F and a keyboard 102G are connected to the calculator 102A. Data can be entered into the calculator 102A by means of the mouse 102F or the keyboard 102G so that the size of an image of the three-dimensional inspection data 401 on the display screen is increased or reduced to any size. In addition, data can be entered into the calculator 102A by means of the mouse 102F or the keyboard 102G so that the color and transparency of the image of the three-dimensional inspection data 401 are optionally changed. The color of the image on the display screen can be changed according to a reflection intensity of wave. In this case, an inspector can select a color pattern from among multiple color patterns on the basis of the purpose of use.

Three-dimensional writing algorithms that are used to display the three-dimensional inspection data are achieved in libraries such as OpenGL (registered trademark) and DirectX (registered trademark). OpenGL and DirectX are industry-standard graphics application programming interfaces (graphics APIs) for graphics applications. When the graphics APIs are used in a program, and necessary information such as the shape of an object to be displayed, a viewpoint and the position of the object to be displayed is provided, the position, color, transparency and size of the image of the three-dimensional inspection data can be selected, and the three-dimensional inspection data can be displayed on the three-dimensional display screen 103C.

As shown in FIG. 5, the display unit 103 can simultaneously display the three-dimensional inspection data 401 and three-dimensional shape data 501 on the three-dimensional display screen 103C. The three-dimensional shape data 501 indicates the shape of the object 100 to be inspected. The inspector can use the mouse 102F or the keyboard 102G and enter data so that the color and transparency of an image of the three-dimensional shape data 501 are changed. In addition, the inspector can enter a value by using the keyboard 102G or drag the three-dimensional shape data 501 by using the mouse 102F so that the three-dimensional shape data 501 can be moved in parallel or rotated on the three-dimensional display screen 103C. In addition, the inspector can switch between displaying of the three-dimensional shaped data 501 and hiding of the three-dimensional shaped data 501 when necessary. Thus, the inspector can easily view the three-dimensional inspection data 401 even when the three-dimensional inspection data 401 and the three-dimensional shape data 501 overlap each other.

When CAD data on the object 100 to be inspected is present as the three-dimensional shape data, the CAD data can be read from the outside of the calculator 102A to be displayed. The format of the CAD data is a data format that allows the CAD data to be input and output by commercially available CAD software. For example, the format of the CAD data is stereolithography (STL) format or stand triangulated language (STL) format. STL formats allow the CAD data to be input and output by many types of CAD software. The format of the CAD data is STL format and represents surfaces of an object by using a group of many triangles. Surface normal vectors of the triangles and coordinate values of the three corners of each of the triangles are written in a STL file. The three-dimensional shape data 501 can be easily read from the STL file and displayed using the graphics APIs by writing multiple triangles.

Normally, a coordinate system of the three-dimensional inspection data 401 is different from that of the three-dimensional shape data 501. Thus, when the three-dimensional inspection data 401 and the three-dimensional shape data 501 are initially displayed, the three-dimensional inspection data 401 and three-dimensional shape data 501 are located at different positions on the three-dimensional display screen 103C as shown in FIG. 6. The inspector can control by trial and error by using the keyboard 102G and enter values or use the mouse 102F so that the three-dimensional inspection data 401 and the three-dimensional shape data 501 are located at desired positions on the three-dimensional display screen 103C. However, this operation takes a long time and is cumbersome. A position adjustment process according to the present invention makes this operation easier.

The position adjustment process is performed by the ultrasonic inspection device according to the present embodiment. The process of position adjustment of the three-dimensional inspection data 401 and the three-dimensional shape data 501 is described below with reference to FIGS. 7 to 10.

Figure 7:
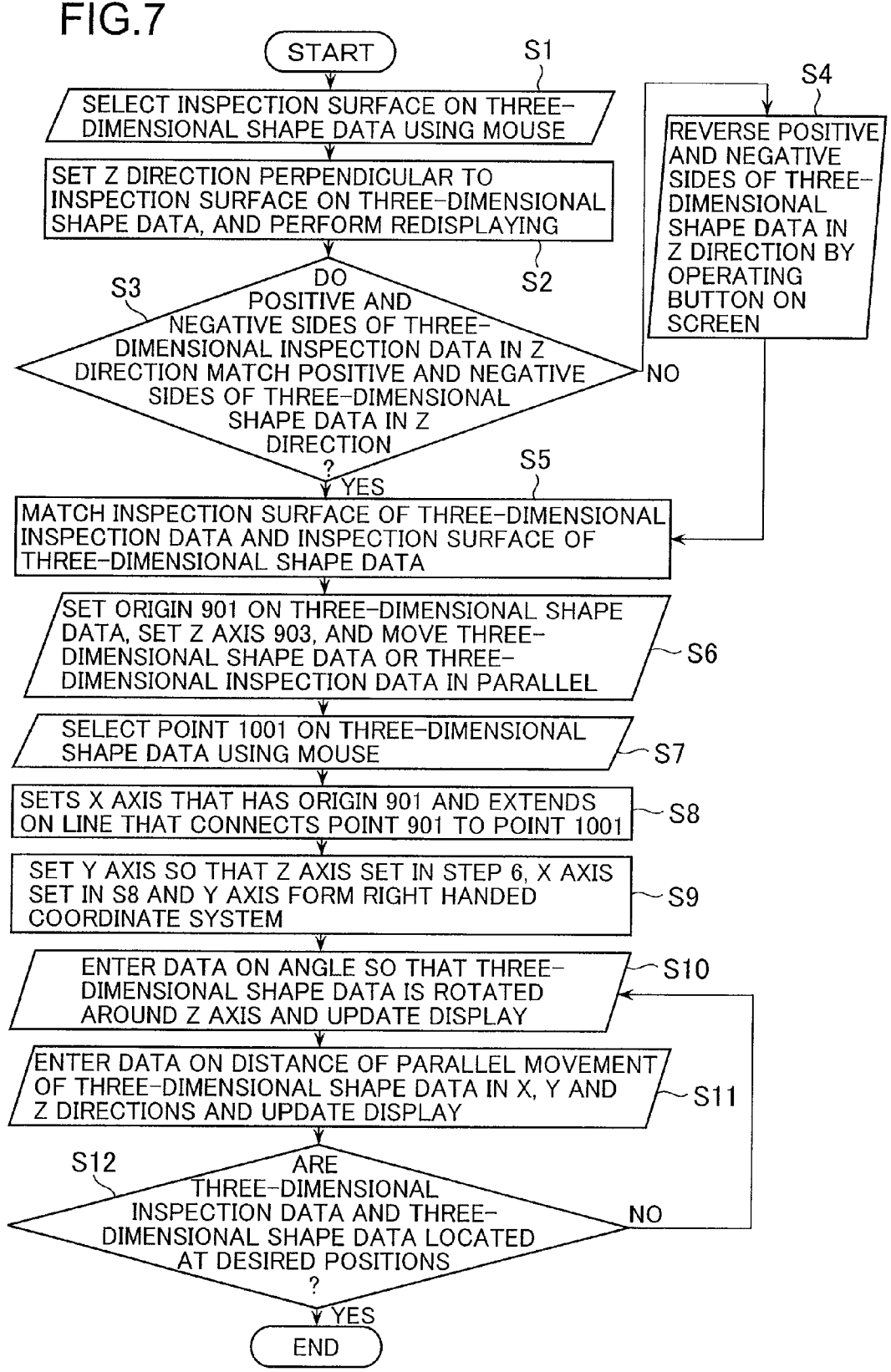
FIG. 7 is a flowchart of a process of position adjustment of three-dimensional inspection data and three-dimensional shape data by the ultrasonic inspection device according to the embodiment of the present invention.
Figure 8:
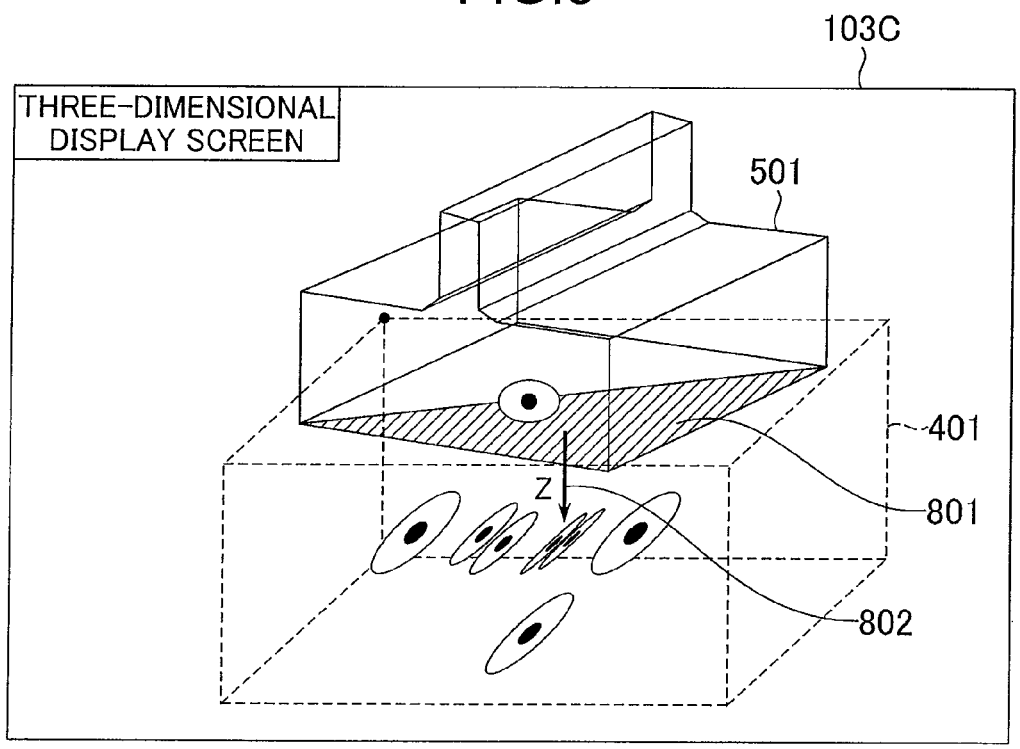
FIG. 8 is a diagram showing an operation during the process of position adjustment of the three-dimensional inspection data and the three-dimensional shape data by the ultrasonic inspection device according to the embodiment of the present invention.
Figure 9:
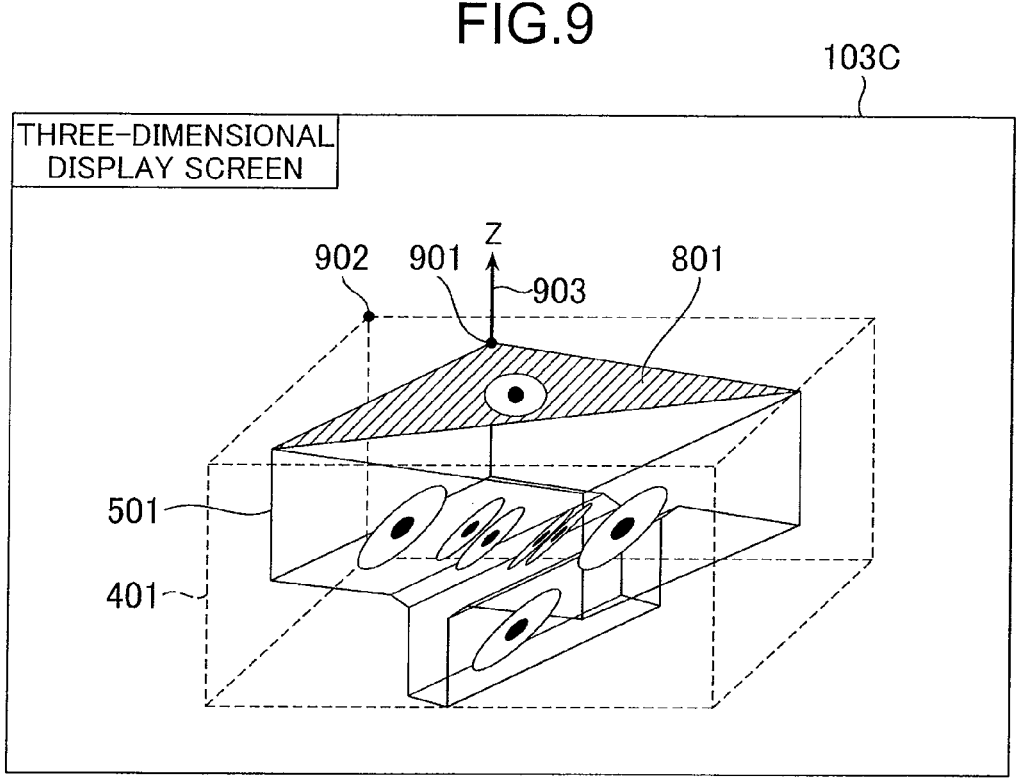
FIG. 9 is a diagram showing an operation during the process of position adjustment of the three-dimensional inspection data and the three-dimensional shape data by the ultrasonic inspection device according to the embodiment of the present invention.
Figure 10:
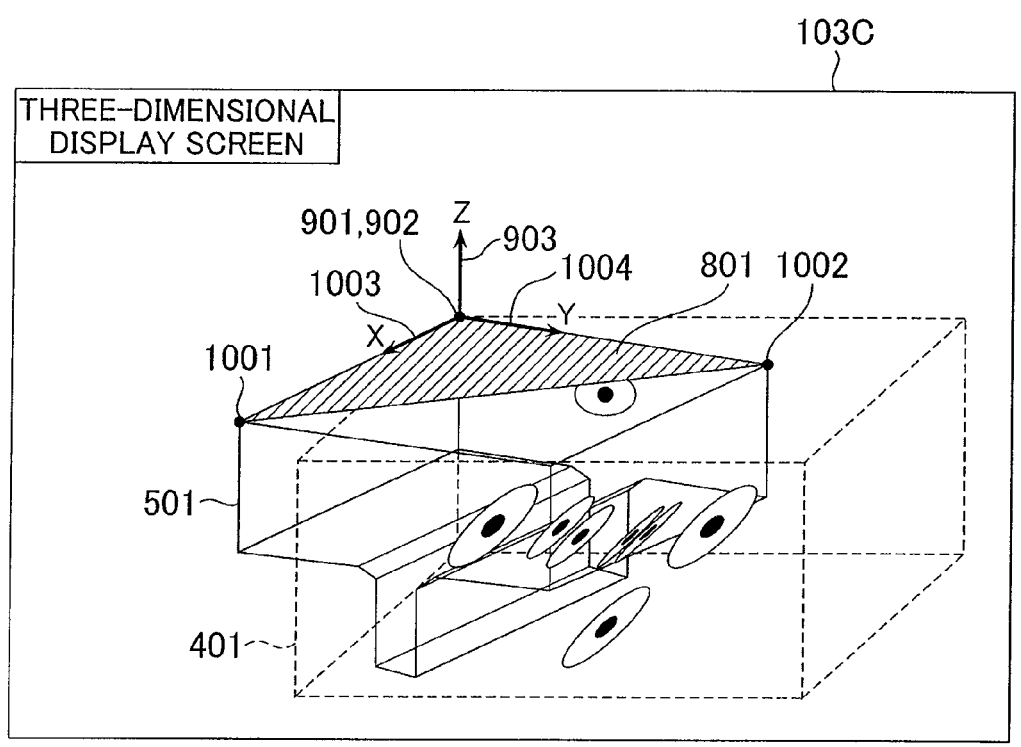
FIG. 10 is a diagram showing an operation during the process of position adjustment of the three-dimensional inspection data and the three-dimensional shape data by the ultrasonic inspection device according to the embodiment of the present invention.

FIG. 7 is a flowchart of the process of position adjustment of the three-dimensional inspection 401 and the three-dimensional shape data 501 by the ultrasonic inspection device according to the present embodiment. FIGS. 8 to 10 are diagrams each showing an operation during the process of position adjustment of the three-dimensional inspection data and the three-dimensional shape data by the ultrasonic inspection device according to the present embodiment.

In general, in order to appropriately position images of two data pieces, a standard coordinate system is set, and parallel movements and rotations are performed. The coordinate system of any of the two data pieces is set as the standard coordinate system in many cases. However, any coordinate system may be set as the standard coordinate system. The scale sizes of the images of the two data pieces match each other. In order to move the data piece in parallel, it is necessary to determine a vector that indicates the amount of the movement and the direction of the movement. In addition, in order to rotate the data piece, it is necessary to determine a rotational axis and a rotational angle.

In the present embodiment, the inspector sets a desired coordinate system on the three-dimensional shape data 501 and uses the mouse 102F or the keyboard 102G to enter positional information in which the set coordinate system is used as a standard coordinate system so that position adjustment is interactively performed.

The position adjustment process according to the present embodiment is described with reference to FIG. 7. The position adjustment process is performed by the calculator 102A. Data on the details of the position adjustment process are stored as a program in the ROM 102A3. The CPU 102A1 reads necessary external data from the data storage unit 102E according to the program stored in the ROM 102A3 or receives data from the RAM 102A2 and executes arithmetic processing on the received data so that an image displayed on the three-dimensional display screen 103C (included in the display unit 103) is changed. In this manner, the CPU 102A1 adjusts the position of the three-dimensional inspection data 401 and the position of the three-dimensional shape data 501 on the three-dimensional display screen 103C.

In step S1, the inspector uses the mouse 102F (connected to the calculator 102A), clicks the inspection surface displayed on the three-dimensional display screen 103C, and thereby selects the inspection surface that is included in the three-dimensional shape data 501 displayed on the three-dimensional display screen 103C. As described above, the array type ultrasonic probe 101 has been placed on the inspection surface. The format of the three-dimensional shape data 501 is STL format. Thus, the displayed three-dimensional shape data 501 is constituted by multiple triangles. The inspection surface is also constituted by multiple triangles. Thus, the inspection surface is selected by selecting a single triangle 801 by using the mouse 102F, as shown in FIG. 8. The triangle 801 constitutes a part of the inspection surface.

Next, in step S2, the calculator 102A defines, on the basis of the information input in step S1, a Z direction 802 that is perpendicular to the inspection surface of the three-dimensional shape data 501, as shown in FIG. 8. Since the three-dimensional inspection data 401 includes positional information on the inspection surface, step S2 can be achieved by simple coordinate conversion.

A surface other than the inspection surface may be selected. When a geometric relationship between a certain surface and the inspection surface is known, the certain surface may be selected in step S1, and a direction that is perpendicular to the certain surface may be defined in step S2.

Next, in step S3, the inspector visually confirms, on the basis of images redisplayed in step S2 on the three-dimensional display screen 103C, whether or not positive and negative sides of the three-dimensional inspection data 401 in the Z direction 802 match positive and negative sides of the three-dimensional shape data 501 in the Z direction 802. As shown in FIG. 8, the positive and negative sides of the three-dimensional inspection data 401 in the Z direction 802 are on the opposite side of the positive and negative sides of the three-dimensional shape data 501 in the Z direction 802 in some cases. In this case, at least one of the three-dimensional inspection data 401 and the three-dimensional shape data 501 is not displayed at a desired position.

When the positive and negative sides of the three-dimensional inspection data 401 in the Z direction 802 are on the opposite side of the positive and negative sides of the three-dimensional shape data 501 in the Z direction 802, the inspector uses the mouse 102F or the keyboard 102G to operate a button on the screen in step S4. Thus, the calculator 102A rotates the three-dimensional shape data 501 180 degrees with respect to the inspection surface so that the positive and negative sides of the three-dimensional shape data 501 in the Z direction 802 are reversed.

When the positive and negative sides of the three-dimensional inspection data 401 in the Z direction 802 match the positive and negative sides of the three-dimensional shape data 501 in the Z direction 802 in step S3 or when the positive and negative sides of the three-dimensional shape data 501 in the Z direction are reversed in step S4, the calculator 102A causes the display unit 103 to redisplay the three-dimensional inspection data 401 and the three-dimensional shape data 501 so that a surface that includes an incident point in the three-dimensional inspection data 401 matches the inspection surface included in the three-dimensional shape data 501. FIG. 9 shows the state in which the three-dimensional inspection data 401 and the three-dimensional shape data 501 are redisplayed.

Next, in step S6, when the inspector uses the mouse 102F and clicks to select a predetermined point 901 located on the three-dimensional shape data 501 on the three-dimensional display screen 103C, the calculator 102A sets a Z axis 903 that has an origin that is located at the point 901. The predetermined point 901 is included in the three-dimensional shape data 501 and corresponds to a corner of the object 100 to be inspected, for example. In addition, the calculator 102A moves the three-dimensional inspection data 401 or the three-dimensional shape data 501 in parallel so that an origin 902 of the three-dimensional inspection data 401 matches the point 901. FIG. 10 shows the state of the three-dimensional display screen 103C after the parallel movement.

Next, in step S7, the inspector uses the mouse 102F and clicks to select a predetermined point 1001 located on the three-dimensional data 501 on the three-dimensional display screen 103C. The point 1001 is included in the three-dimensional shape data 501 and corresponds to a corner of the object 100 to be inspected, for example.

After step S7 is performed, the calculator 102A sets an X axis 1003 that has an origin that is located at the point 901 in step S8, while the X 1003 axis extends on a line that connects the point 901 to the point 1001.

Next, in step S9, the calculator 102A automatically sets a Y axis so that the X axis set in step S8, the Z axis set in step S6 and the Y axis form a right handed coordinate system. In this case, the origin of the coordinate system is the point 901.

In steps S1 to S9, the inspector sets the new desired coordinate system on the three-dimensional shape data 501. This coordinate system can be set using the characteristic shape of the object 100 (to be inspected) as a standard that is used for an actual measurement in the case where data on the position of the array type ultrasonic probe 101 is stored. Normally, a corner of the object 100 to be inspected or the like is set as the origin of the coordinate system. In addition, normally, sides of the object 100 to be inspected, which include the corner or the like, are set as the X and Y axes. Since the coordinate system is set in the aforementioned manner, the inspector sets the position of the array type ultrasonic probe 101 relative to the three-dimensional shape data 501, with a feeling similar to that in an actual measurement.

After the coordinate system is set, the calculator 102A rotates the three-dimensional inspection data 401 or the three-dimensional shape data 501 relative to the other image around the Z axis 903 on the basis of information that indicates a rotational angle and has been input using the mouse 102F or the keyboard 102G so that the calculator 102A updates the display in step S10.

Next, in step S11, the calculator 102A moves the three-dimensional inspection data 401 or the three-dimensional shape data 501 in parallel relative to the other data along the X axis 1003, the Y axis 1004 and the Z axis 903 on the basis of information that indicates the amount of the parallel movement and has been input using the mouse 102F or the keyboard 102G so that the calculator 102A updates the display. Step S11 may be performed after step S12.

Lastly, in step S12, the inspector visually confirms whether or not the three-dimensional inspection data 401 and the three-dimensional shape data 501 are located at desired positions on the three-dimensional display screen 103C. When the three-dimensional inspection data 401 and the three-dimensional shape data 501 are not located at the desired positions, steps S10 and S11 are repeated.

In the process, the three-dimensional inspection data 401 and the three-dimensional shape data 501 can be appropriately positioned in an efficient manner.

As described above, in the present embodiment, it is possible to appropriately position the three-dimensional inspection data 401 and the three-dimensional shape data 501 on the display screen and quickly identify a defect echo and a shape echo.

Next, the configuration and operations of an ultrasonic inspection device according to another embodiment of the present invention are described with reference to FIG. 11.

Figure 11:
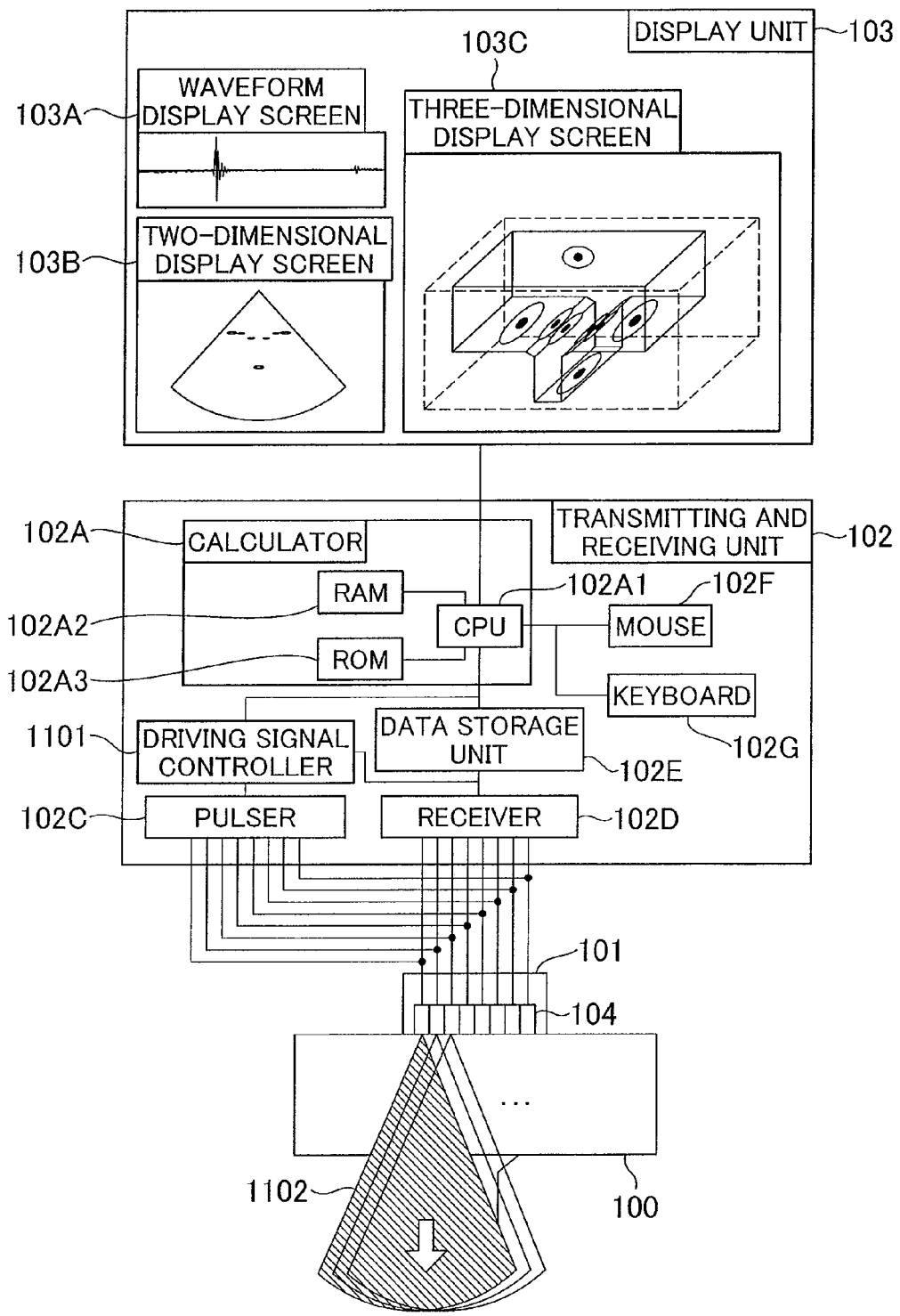
FIG. 11 is a block diagram showing the entire configuration of an ultrasonic inspection device according to another embodiment of the present invention.

FIG. 11 is a block diagram showing the entire configuration of the ultrasonic inspection device according to the other embodiment of the present invention. In FIG. 11, the same reference numerals as in FIG. 1 indicate the same parts as in FIG. 1.

In the embodiment shown in FIG. 1, it is assumed that the three-dimensional inspection data 401 is acquired by the phased array method. In the present invention, three-dimensional inspection data that is acquired by a method other than the phased array method can be used. For example, three-dimensional inspection data that is acquired by an aperture synthesis method can be used, as described below with reference to FIG. 11.

The ultrasonic inspection device (shown in FIG. 11) according to the present embodiment includes the array type ultrasonic probe 101, the transmitting and receiving unit 102 and the display unit 103. The array type ultrasonic probe 101 transmits ultrasonic waves so that the ultrasonic waves are incident on the object 100 to be inspected. The display unit 103 displays received signals and an image (inspection image) on the object 100 to be inspected.

The array type ultrasonic probe 101 has a plurality of piezoelectric elements 104 that each generate and receive an ultrasonic wave as shown in FIG. 11. After the array type ultrasonic probe 101 is placed on the inspection surface of the object 100, the array type ultrasonic probe 101 receives driving signals from the transmitting and receiving unit 102, generates ultrasonic waves 1102 on the basis of the driving signals, and causes the ultrasonic waves 1102 to propagate in the object 100 to be inspected. Then, the array type ultrasonic probe 101 detects, as received signals, the waves reflected from the object 100. The array type ultrasonic probe 101 transmits the received signals to the transmitting and receiving unit 102.

The piezoelectric elements 104 included in the array type ultrasonic probe 101 are sequentially driven at predetermined times by means of driving signals transmitted from a driving signal controller 1101 through the pulser 102C. The piezoelectric elements 104 receive, as signals, the reflected ultrasonic waves that have been transmitted from the piezoelectric elements 104. The received signals are input to the receiver 102D. Specifically, the piezoelectric elements 104 included in the array type ultrasonic probe 101 receive the reflected waves as much as the total number thereof.

The signals input to the receiver 102D are sequentially stored in the data storage unit 102E as storage data. The calculator 102A converts the waveforms of the waves received by the piezoelectric elements 104 into a three-dimensional image by using the storage data and an aperture synthesis method. Then, the calculator 102A causes the display unit 103 to display the three-dimensional image.

The calculator 102A basically includes a CPU 102A1, a RAM 102A2 and a ROM 102A3. A program that controls the CPU 102A1 is written in the ROM 102A3. The CPU 102A1 reads necessary external data from the data storage unit 102E according to the program written in the ROM 102A3. In addition, the CPU 102A1 receives data from the RAM 102A2, executes arithmetic processing on the received data, and outputs the processed data to the data storage unit 102E when necessary.

In this manner, the calculator 102A generates the three-dimensional inspection data 401 by using the aperture synthesis method. A method for position adjustment and displaying of the three-dimensional inspection data 401 generated using the aperture synthesis method with the three-dimensional shape data 501 is the same as or similar to the method described with reference to FIGS. 7 to 10.

In the present embodiment, it is possible to easily adjust the position of the three-dimensional inspection data and the position of the three-dimensional shape data on the display screen and quickly identify a defect echo and a shape echo.

What is claimed is:
1. An ultrasonic inspection device comprising:
   an ultrasonic probe which provides a plurality of piezoelectric elements;
   a pulser which supplies transmission signals to the respective piezoelectric elements of the ultrasonic probe;
   a receiver which receives signals from the respective piezoelectric elements of the ultrasonic probe;
   a delay time controller which sets delay times to the transmission signals to be supplied to the piezoelectric elements and sets delay times to the signals received by the piezoelectric elements, the delay times set to the trans- mission signals being different from each other, the delay times set to the received signals being different from each other;

a data storage unit which stores the waveforms of ultrasonic waves received by the ultrasonic probe;

a calculator which is provided for image processing and which generates three-dimensional inspection data from the waveforms stored in the data storage unit;

a three-dimensional display unit which displays three-dimensional shape data of an object to be inspected and the three-dimensional inspection data generated by the calculator; and a positioning correction section which corrects the relative positions of the displayed three-dimensional shape data and the displayed three-dimensional inspection data on the basis of a coordinate system defined by points and a surface represented by a part of the three-dimensional shape data displayed by the three-dimensional display unit, the positioning correction section being used to display the three-dimensional shape data and the three-dimensional inspection data while the three-dimensional shape data and the three-dimensional inspection data overlap each other, wherein the positioning correction section:

defines a Z direction that is perpendicular to an inspection surface on which the ultrasonic probe has been placed, the inspection surface having been selected from the three-dimensional shape data displayed on the three-dimensional display unit;

redisplays the three-dimensional shape data and the three-dimensional inspection data, after positive and negative sides of the three-dimensional inspection data displayed on the three-dimensional display unit in the Z direction match positive and negative sides of the three-dimensional shape data displayed on the three-dimensional display unit in the Z direction, so that a surface that provides an incident point in the three-dimensional inspection data matches the inspection surface of the three-dimensional shape data;

sets a Z axis that has an origin that is a first point which is located on, , and selected from the three-dimensional shape data;

moves one of the three-dimensional inspection data and the three-dimensional shape data in parallel so that the origin of the three-dimensional inspection data matches the first point;

sets an X axis that has an origin that is the first point, wherein the X axis extends on a line that connects the first point to a second point which is located on, and selected from, the three-dimensional shape data;

sets a Y axis so that the X, Y and Z axes form a right handed coordinate system;

rotates the one of the three-dimensional inspection data and the three-dimensional shape data relative to the other data around the Z axis on the basis of input information on a rotational angle and updates the three-dimensional display unit; and moves the one of the three-dimensional inspection data and the three-dimensional shape relative to the other data in parallel along the X, Y and Z axes on the basis of input information on the amount of the parallel movement and updates the three-dimensional display unit.

2. The ultrasonic inspection device according to claim 1, wherein the surface which is represented by a part of the three-dimensional shape data, and which corresponds to a surface on which the ultrasonic probe has been placed, is selected in order to store the waveforms of the ultrasonic waves.

3. The ultrasonic inspection device according to claim 1, further comprising a mouse which is connected to the calculator, wherein the points and the surface, which are represented by the part of the three-dimensional shape data, are selected with the mouse.

4. An ultrasonic inspection method comprising the steps of:

correcting the relative displayed positions of three-dimensional shape data and three-dimensional inspection data on the basis of a coordinate system defined by points and a surface represented by a part of the three-dimensional shape data, the three-dimensional inspection data being generated from a plurality of waveforms of ultrasonic waves received by an ultrasonic probe;

displaying the three-dimensional shape data and the three-dimensional inspection data while the three-dimensional shape data and the three-dimensional inspection data overlap each other;

defining a Z direction that is perpendicular to an inspection surface on which the ultrasonic probe has been placed, the inspection surface being selected from the three-dimensional shape data displayed on a three-dimensional display screen;

redisplaying the three-dimensional shape data and the three-dimensional inspection data, after positive and negative sides of the three-dimensional inspection data displayed on the three-dimensional display screen in the Z direction match positive and negative sides of the three-dimensional shape data displayed on the three-dimensional display screen in the Z direction, with a surface that provides an incident point in the three-dimensional inspection data matching the inspection surface of the three-dimensional shape data;

setting a Z axis that has an origin that is a first point which is located on, and selected from the three-dimensional shape data;

moving one of the three-dimensional inspection data and the three-dimensional shape data in parallel so that the origin of the three-dimensional inspection data matches the first point;

setting an X axis that has an origin that is the first point, the X axis extending on a line that connects the first point to a second point which is located on, and selected from the three-dimensional shape data;

setting a Y axis so that the X, Y and Z axes form a right handed coordinate system;

rotating the one of the three-dimensional inspection data and the three-dimensional shape data relative to the other data around the Z axis on the basis of input information on an rotational angle and updating the three-dimensional display screen; and moving one of the three-dimensional inspection data or the three-dimensional shape relative to the other data in parallel along the X, Y and Z axes on the basis of input information on the amount of the parallel movement and updating the three-dimensional display screen.

5. The ultrasonic inspection method according to claim 4 further including;

selecting the surface represented by a part of the three-dimensional shape data to correspond to a surface on which the ultrasonic probe has been placed in order to store the waveforms of the ultrasonic waves.

6. The ultrasonic inspection method according to claim 4 further including;
    selecting the points and the surface represented by the part of the three-dimensional shape data using a mouse.

* * * * *